(12) United States Patent
York (10) Patent No.: US 9,649,398 B1
(45) Date of Patent: May 16, 2017

(54) METHOD AND APPARATUS FOR SANITIZING DOOR KNOBS OR DOOR HANDLES

(71) Applicant: Darren York, Old Bridge, NJ (US)

(72) Inventor: Darren York, Old Bridge, NJ (US)

(*) Notice: Subject to any disclaimer, the term of this patent is extended or adjusted under 35 U.S.C. 154(b) by 0 days.

(21) Appl. No.: 15/341,400

(22) Filed: Nov. 2, 2016

(51) Int. Cl.
*A61L 2/10* (2006.01)
*A61L 2/24* (2006.01)

(52) U.S. Cl.
CPC ...... *A61L 2/24* (2013.01); *A61L 2/10* (2013.01); *A61L 2202/14* (2013.01)

(58) Field of Classification Search
CPC ................................. A61L 2/10; A61L 2/24
See application file for complete search history.

(56) References Cited

U.S. PATENT DOCUMENTS

| | | | |
|---|---|---|---|
| 4,710,634 A | 12/1987 | Brookes | |
| 6,298,521 B1 | 10/2001 | Butterfield | |
| 7,175,807 B1 | 2/2007 | Jones | |
| 7,989,779 B1 | 8/2011 | Ray et al. | |
| 2006/0153733 A1 | 7/2006 | Sassoon | |
| 2006/0175843 A1 | 8/2006 | Campopiano et al. | |
| 2010/0140499 A1* | 6/2010 | Casale | E05B 1/0069 250/454.11 |
| 2011/0174992 A1* | 7/2011 | Sakita | A61L 2/10 250/492.1 |
| 2012/0305804 A1* | 12/2012 | Goldman | E05B 1/0069 250/492.1 |
| 2014/0048724 A1* | 2/2014 | Marshall | E05B 1/0069 250/492.1 |
| 2014/0137369 A1 | 5/2014 | Street | |
| 2016/0263263 A1* | 9/2016 | Robert | A61L 2/14 |

* cited by examiner

*Primary Examiner* — Sean E Conley
(74) *Attorney, Agent, or Firm* — Walter J. Tencza, Jr.

(57) ABSTRACT

An apparatus including a first apparatus for producing light, which may include a first device for detecting movement of a door, and a first set of one or more light sources. The first set of one or more light sources may be configured to turn on when the first device for detecting movement of the door detects movement of the door. The first set of one or more light sources are configured to produce short wavelength ultraviolet light. The first device for detecting movement of the door may include an accelerometer. The first apparatus for producing light may include a computer processor; a computer memory; having a stored threshold value. The computer processor may compare a value of a detected signal produced with the threshold value and to cause the first set of one or more light sources to be turned on if the detected signal exceeds the threshold value.

1 Claim, 9 Drawing Sheets

METHOD AND APPARATUS FOR SANITIZING DOOR KNOBS OR DOOR HANDLES

FIELD OF THE INVENTION

This invention relates to improved methods and apparatus for sanitizing door knobs or door handles.

BACKGROUND OF THE INVENTION

While there are existing patents that try to solve the spreading of germs on a door knob/handle, none are practical or commercially viable. Many known previous devices are stand-alone units that replace an existing door knob/handle. This presents at least two problems: first, it is not a quick and easy install, eliminating a portion of the population that is willing to install the device themselves; secondly, it limits the market considerably, as individuals are forced to accept the aesthetics of a device that contain the packaged door knob/handle instead of using their existing door knob/handle in a retrofit application. For instance, some previous patents are stand-alone devices only in the shape of a doorknob. This limits the market as those who have door handles will likely not use that product.

Previous patents only addressed one side of the door knob/handle. While an additional device can be placed on the opposite side of the door, there is no direct communication or sequencing that allows this device to effectively eliminate microorganisms on both sides of the door, given the possibility that only one side of the door is sanitized defeating the purpose of the product; stopping the spreading of germs through contact with door knobs/handles. To provide a pragmatic and effective solution, both sides of the door would need to be sanitized.

Many previous patents disclose devices which are mechanical in nature which presents maintenance issues, increases the weight, and adds to bulkiness of the device while consuming significantly more energy.

Using an infrared sensing device as indicated in a previous patent is an imperfect solution, as the dominant hand of the person opening the door could be on the opposite side of the sensing device and hence not sensed. Infrared sensing devices have other issues that can lead to devices disclosed in previous patents not functioning as intended all the time.

SUMMARY OF THE INVENTION

In at least one embodiment, an electronic doorknob/handle sanitizer apparatus is provided designed and engineered to combat the spreading of germs using UVC (ultraviolet C) light to destroy microorganisms on a door handle or door knob surfaces. UVC light has a wavelength typically between one hundred and two hundred and eighty nanometers, inclusive, and a photon energy between 4.43 and 12.4 eV (electronvolts), or between 0.710 and 17.987 aJ (attojoules), and is short-wave germicidal, and typically fully absorbed by the atmosphere and the ozone layer.

The apparatus may include two sequenced communicating sanitizers that operate on the inside and outside of any given door. The apparatus may be used on existing doorknobs/handles in a retrofit application. The apparatus may include an accelerometer that detects movement on a door; when open or closed, and communicates that signal to the controller located on an electronic circuit board of one of the sanitizers. That sanitizer in turn may communicate via Bluetooth to the sanitizer located on the opposite side of the door enabling the built in LED (light emitting diode) UV-C lights of both sanitizers on a five-second delay. A Lithium Ion battery may be used to power the LED UV-C lights for about twenty seconds sanitizing the surface of the doorknob/handle. In at least one embodiment, the apparatus has been found to be 99% effective at destroying microbes at a distance of three inches. The UV-C light is projected in a conical shape towards the doorknob or handle and the apparatus may have an under mounted mirror to reflect UV light towards the underside of the doorknob/handle. The apparatus may be affixed to a door surface using two-sided removable tape identified in drawings, sitting approximately one and a half inches above a doorknob surface. Using two-sided tape allows the device to be removable and easily reapplied if necessary. The apparatus may operate using a rechargeable lithium-ion battery. The LED UV-C bulb used may have a estimated life of 10,000 hours.

One or more embodiments provide a true retrofit application, where there is no need to change or modify the existing door; no need to sacrifice function above form. In addition, one or more embodiments allow both sides of the door knob/handle to be sanitized in a sequenced fashion while eliminating redundant controllers and motion sensing devices.

One or more embodiments of the present invention eliminate redundancy, miniaturizes the application, and creates a layer of safety (to not expose people's hands to UV light) not previously addressed. By sequencing the sanitizing of the door knob/handle by a programmed controller communicating via Bluetooth or equivalent communication standard, and activated by a built-in accelerometer, the devices on either side of the door synchronize the dispersion of UV-C light on the door knobs/handles. One or more embodiments create a more practical, efficient, safe, and effective deliverance of a sanitized door knob/handle.

One or more embodiments of the present invention are electronic with virtually no moving parts. Energy consumption is reduced, improving battery life along with the application of LED UVC light instead of implied low-pressure sodium lights. LED UV-C lights also eliminate a need for a ballast which would have had to be included in previous designs.

One or more embodiments of the present invention are more energy efficient, require no maintenance, and are considerably lighter allowing the device to be affixed using double sided tape. One or more embodiments of the present invention can be easily removed and relocated without any damage to the door.

One or more embodiments of the present invention provide an accelerometer, which, in some embodiments, is a perfect solution to accurately sense when the door needs to be sanitized, as a force is applied whenever a door moves open or closed. The accelerometer responds to this force (movement) and is a preferred way that an apparatus can accurately detect when sanitizing needs to be applied.

The underside reflector is incorporated to reflect the sterilizing UV light from the device onto the underside of the door knob/handle. The reflector is conforms to the circular shape of the mounting plate/bracket of the door knob or handle. With the reflector, the device properly addresses sterilizing the entire door knob/handle and not just the top surface.

In at least one embodiment of the present application an apparatus is provided comprising a first apparatus for producing light, wherein the first apparatus for producing light includes a first device for detecting movement of a door; wherein the first apparatus for producing light includes a first set of one or more light sources; wherein the first set of one or more light sources are configured to turn on when the first device for detecting movement of the door detects movement of the door; and wherein the first set of one or more light sources are configured to produce short wavelength ultraviolet light.

The first device for detecting movement of the door may include an accelerometer. The apparatus may include the door itself; and the first device for detecting movement of the door may be fixed to the door.

The apparatus may include a computer processor; and a computer memory; wherein the computer memory has stored therein a threshold value; and wherein the computer processor is programmed to compare a value of a detected signal produced by the first device for detecting movement of the door in response to movement of the door, with the first threshold value and to cause the first set of one or more light sources to be turned on if the value of the detected signal exceeds the threshold value.

The first apparatus for producing light may have housing, and the first set of one or more light sources may be fixed to and inside of the housing and configured so that light from the first set of one or more light sources is directed at a first doorknob of the door, when the first set of one or more light sources is turned on, and the housing is fixed to the door.

The overall apparatus may include a second apparatus for producing light; wherein the second apparatus for producing light includes a second set of one or more light sources; wherein the second set of one or more light sources are configured to turn on when the first device for detecting movement of the door detects movement of the door; and wherein the first apparatus for producing light and the second apparatus for producing light are separate and are configured to be fixed to opposite sides of the door; and wherein the first and second set of one or more light sources are configured to produce short wavelength ultraviolet light.

In at least one embodiment, the overall apparatus may include a first apparatus for reflecting light; wherein the first apparatus for producing light and the first apparatus for reflecting light can be fixed to the door and configured so that light emanates from the first apparatus for producing light towards the first apparatus for reflecting light, and is at least partially reflected by the first apparatus for reflecting light back towards the first apparatus for producing light.

In at least one embodiment, the first apparatus for producing light has a housing having a width; the first apparatus for reflecting light has a housing having a width; and the width of the first apparatus for producing light is substantially the same as the width of the first apparatus for reflecting light.

In at least one embodiment the housing of the first apparatus for producing light is fixed to the door, at about one and half inches from the first door knob of the door. The first apparatus for producing light and the first apparatus for reflecting light may be fixed to the door, so that the first door knob is between the first apparatus for producing light and the first apparatus for reflecting light.

In at least one embodiment a method is provided including projecting first light towards a first doorknob of a door in response to movement of the door; and wherein the first light is short wavelength ultraviolet light. The method may include projecting second light towards a second doorknob of the door in response to movement of the door; wherein the first doorknob and the second doorknob are located on opposite sides of the door; and wherein the second light is short wavelength ultraviolet light.

In at least one embodiment, the steps of projecting first light towards the first doorknob of the door and second light towards a second doorknob of the door are performed only if the movement of the door is sufficient to cause a threshold to be exceeded.

A value concerning the threshold may be stored in computer memory, and a computer processor may compare a value of a signal generated by the movement of the door with the value of the threshold stored in computer memory to determine if the threshold has been exceeded. The signal generated by the movement of the door may be generated by an accelerometer. The method may include reflecting at least part of the first light back towards the first doorknob.

The first light may emanate from a first housing wherein the first housing has a width; wherein the at least part of the first light is reflected back from a second housing separate from the first housing; and the method may further include fixing the first housing and the second housing on the door, so that the first doorknob is between the first housing and the second housing.

DETAILED DESCRIPTION OF THE DRAWINGS

Figure 1:
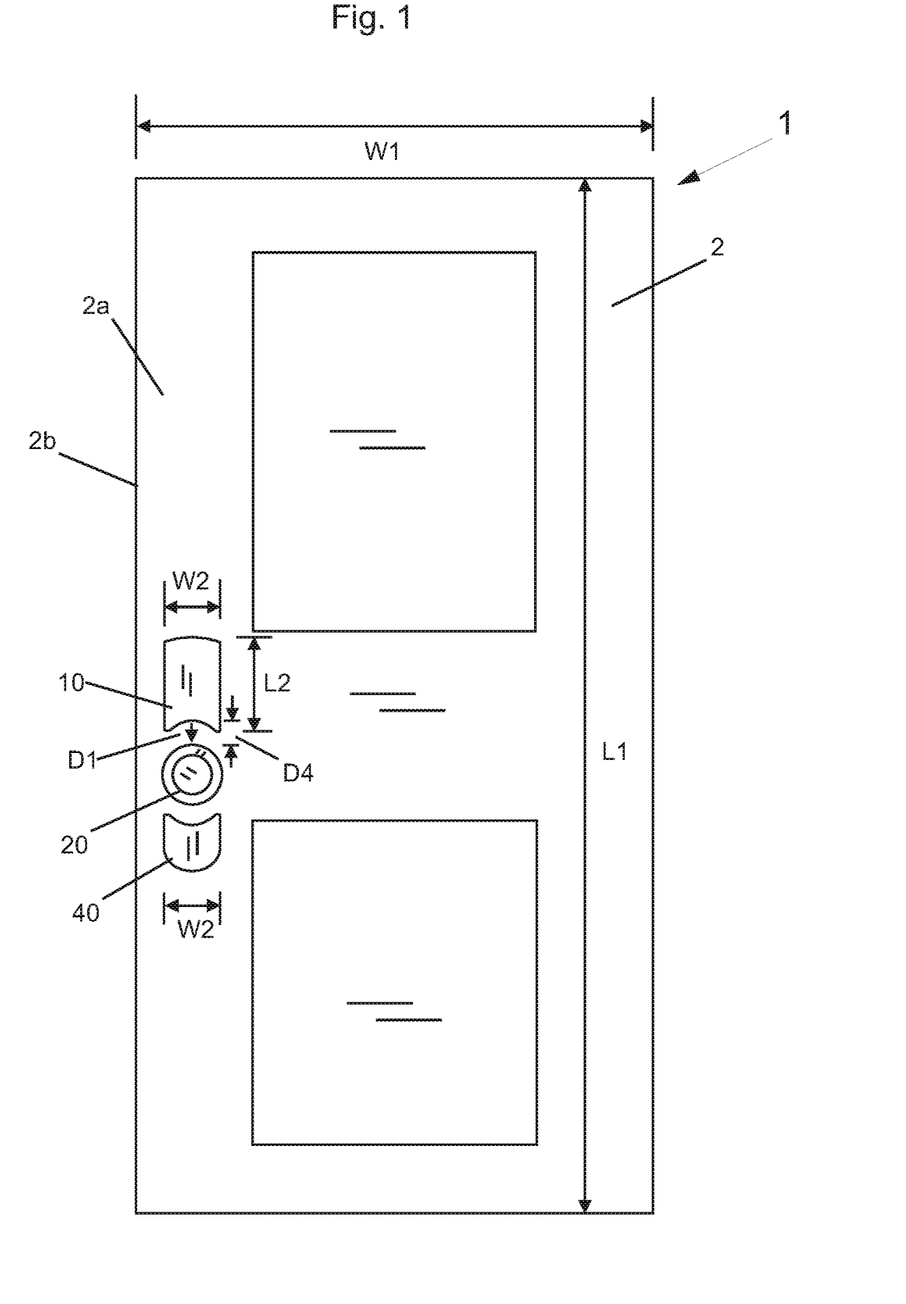
FIG. 1 shows front view of an overall apparatus including a door, a first door handle, a first apparatus produces light, and a first apparatus which reflects light, in accordance with an embodiment of the present invention.

FIG. 1 shows front view of an overall apparatus 1 including a door 2, a first door handle or door knob 20, a first apparatus 10 which produces light, and a first apparatus which reflects light 40, in accordance with an embodiment of the present invention. The door 2 has a front surface 2a, and a left edge 2b. The door may be a solid rectangular door, and may have a width, W1, which may be about one and one half inches and a length L1, which may be about eighty three inches. The first apparatus which produces light 10 may be temporarily fixed to the door surface 2a by an adhesive or by Velcro (trademarked), or by a double sided tape. In at least one embodiment using a double sided tape to fix the first apparatus which produces light 10 to the door is preferred. In at least one embodiment, each of the the first apparatus which produces light 10 and the first apparatus which reflects light 40 is configured to have a width, W2 which is about the same as a diameter D2 of the door knob or handle 20. This allows light, such as ultraviolet light in at least one embodiment, such as preferably UVC light (short wavelength ultraviolet light) emanating out of the first apparatus which produces light 10 in the direction D1, from a bottom opening or region 11e, to substantially encompass the entire diameter D2 of the door knob 20, to be reflected back by reflecting surface 42 of the first apparatus which reflects light 40, and to further encompass the door knob 20 so that the entire or substantially the entire door knob 20 has light directed it on it from the combination of the apparatus 10 and the apparatus 40.

In at least one embodiment, the light emanating from end or side 11e from the apparatus 10 and reflected back the apparatus 40, is typically UVC light, and typically kills all or substantially all germs on all surfaces of the door knob 20, except possibly the face of the door knob 20, wherein the face of the door knob 20 typically does not come in contact with an individual's hand. Having the width W2 of the apparatus 10 and the apparatus 40 be the same as the door knob 20 diameter D2 also creates an aesthetically pleasing look.

The door 2 may be a standard size door, such as having a width W1 of about three feet, and a length L1 of about six and one half feet. The overall apparatus 1 may have a length L2 which may be larger than the width W2. In at least one embodiment, it is critical that the first apparatus for producing light 10 be a distance D4, an inch and a half or less away from the first door knob 20 to provide optimum killing of germs on door knob 20, and also to provide clearance for an individual's hand to turn the door knob 20. In at least one embodiment, a ½ inch is necessary to provide adequate clearance for an individual's hand.

Figure 2:
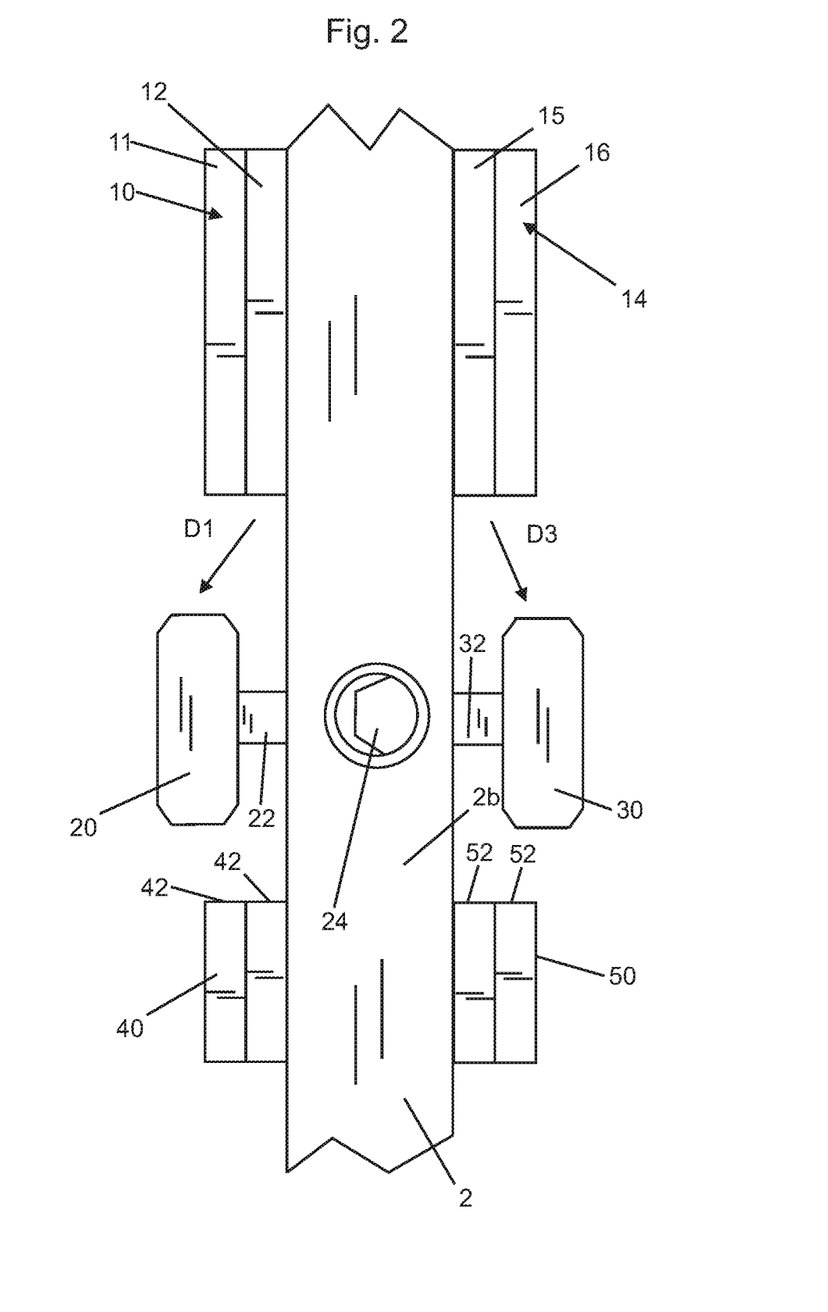
FIG. 2 shows a side view of part of the door in FIG. 1, the first apparatus which produces light, the first apparatus which reflects light of FIG. 1, the first door handle of FIG. 1, a second apparatus which produces light, and a second apparatus which reflects light, and a second door handle in accordance with an embodiment of the present invention.

FIG. 2 shows a side view of part of the door 2 in FIG. 1, the first apparatus 10 which produces ultraviolet light of FIG. 1, the first apparatus which reflects light 40, the first door handle 20 of FIG. 1, a second apparatus 14 which produces light, a second apparatus which reflects light 50, and a second door handle 30 in accordance with an embodiment of the present invention. The edge 2b of the door 2 is visible in FIG. 2. The first apparatus 10 includes a cover 11, and a housing 12, in which various components are located. The second apparatus 14 includes a cover 16 and a housing 15 in which various components are located. The first apparatus 10 and the second apparatus 14 may be identical. The first door handle 20 may be connected by axles 22 and 32 to the second door handle 30. The first door handle 20 and/or the second door handle 30 may turn the locking or latching door mechanism 24 in a known manner. The first and second door handles 20 and 30 may be any known door handles or door knobs, and the locking or latching mechanism may be any known locking or latching mechanism. The first apparatus for reflecting light 40 and the second apparatus for reflecting light 50 may be identical, which each having a reflecting surface or device, such as reflecting surface or device 42 for apparatus 40, and a similar or identical reflecting surface or device 52 for apparatus 50.

The first apparatus 10 may emit UV light in the direction D1, and this light may disinfect the door knob 20 or at least part of the door knob 20, such as a top edge portion. At least part of the light from the first apparatus 10, is directed on the reflecting surface or device 42 and reflected back towards the door knob 20 to disinfect at least part of the door knob 20, such as a bottom edge portion.

The second apparatus 14 may emit UV light in the direction D3, and this light may disinfect the door knob 30 or at least the part of the door knob 30, such as a top edge portion. At least part of the light from the second apparatus for producing light 14, is directed onto the reflecting surface or device 52 and reflected back towards the door knob 30 to disinfect at least part of the door knob 30, such as a bottom edge portion.

Figure 3:
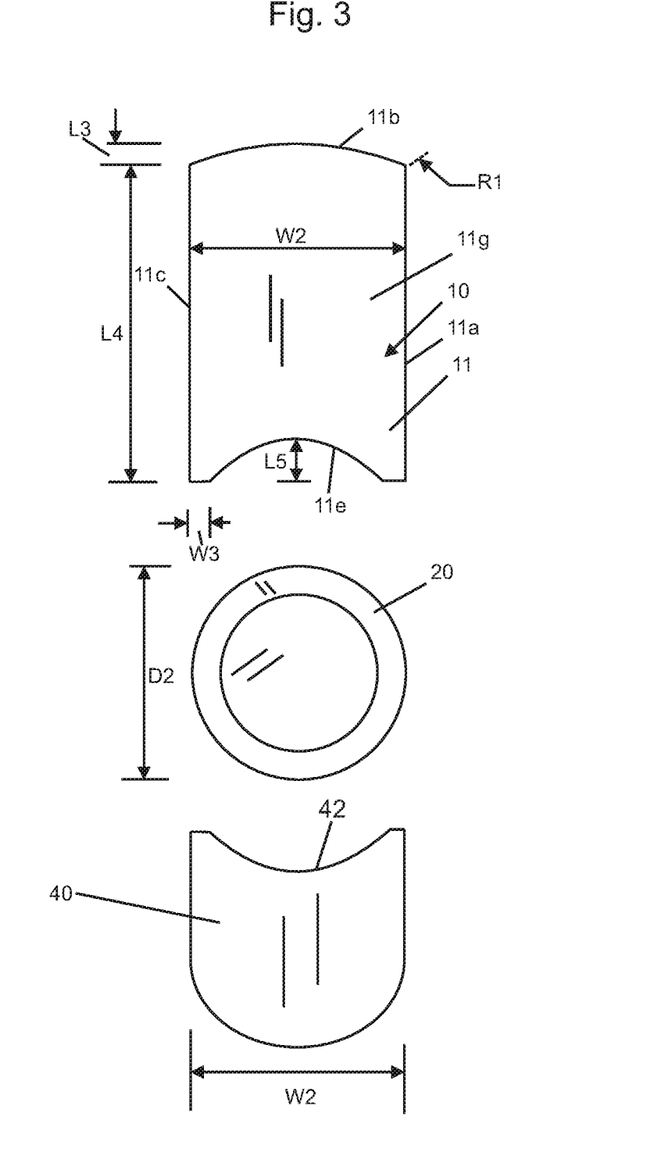
FIG. 3 shows a closeup front view of the first apparatus which produces light of FIG. 1, the first apparatus which reflects light of FIG. 1, and the first door handle of FIG. 1.

FIG. 3 shows a closeup front view of the first apparatus which produces light 10, the first apparatus which reflects light 40 and the first door handle 20. The cover 11 of the first apparatus 10 may have a top edge 11b, a front surface 11g, a left side or wall 11c, a right side or wall 11a, and a bottom region or opening 11e. There are two flat surfaces which has a width W3. The curved top edge 11b, may have a radius of curvature of R1, which may be about ⅝ inches. The distance from the top of top edge 11b, and the start of flat sides or walls 11c and 11a may be L3, which may be about ¼ of an inches. The sides or walls 11c and 11a may have a length L4 of about four inches. The width W2 of the cover 11 may be about two and one half inches, which may be about the same as the diameter D2 of the door knob 20, to provide coverage of the door knob 20 with emitted ultraviolet light from the bottom region or opening 11e.

The distance between the top of bottom region or opening 11e and the bottom end of sides or walls 11c and 11a may be about L5, which may be about one half of an inch. The apparatus for reflecting light 40 may have a width W2 which is equal to the width of the apparatus for producing light 10 to allow light emanating from opening 11e to be receiving sufficiently at reflecting surface 42, and to allow for an aesthetically pleasing appearance with respect to door knob 20.

Figure 4:
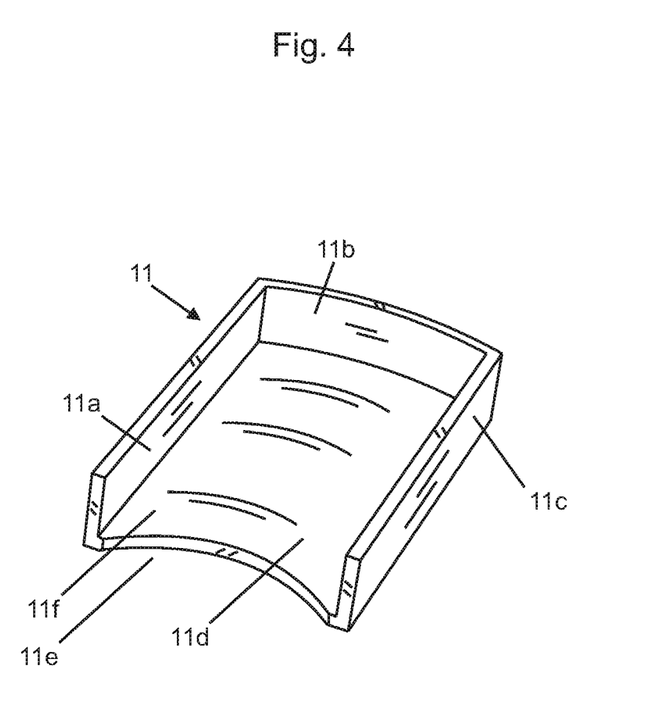
FIG. 4 shows a rear, left, and bottom perspective view of a cover of the first apparatus which produces light of FIG. 1.

FIG. 4 shows a rear, left, and bottom perspective view of a cover 11 of the first apparatus which produces light 10 of FIG. 1. FIG. 4 shows the flat sides or walls 11a and 11c, and top edge or wall 11b. FIG. 4 shows inner surface 11d, and chamber 11f surrounded by walls 11a, 11 b, 11c, and opening, entrance or end 11e.

Figure 5:
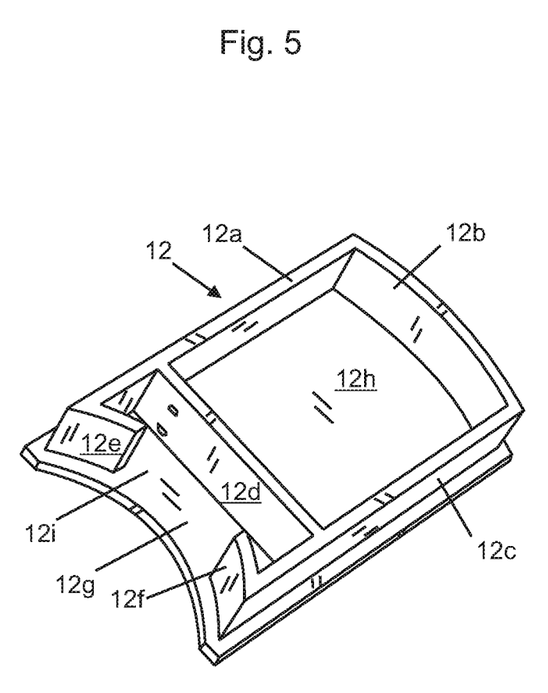
FIG. 5 shows a front, right, and bottom perspective view of a housing of the first apparatus which produces light, wherein the housing is shown without various internal components.

FIG. 5 shows a front, right, and bottom perspective view of a housing 12 of the first apparatus which produces light 10, wherein the housing 12 is shown without various internal components. The housing 12 includes walls or sides 12a, 12b, 12c, 12d, 12e, and 12f. There is an opening 12g, between walls 12e and 12f. There is a chamber or region 12h surrounded by walls 12a, 12b, 12c, and 12d. There is a surface 12i.

Figure 6:
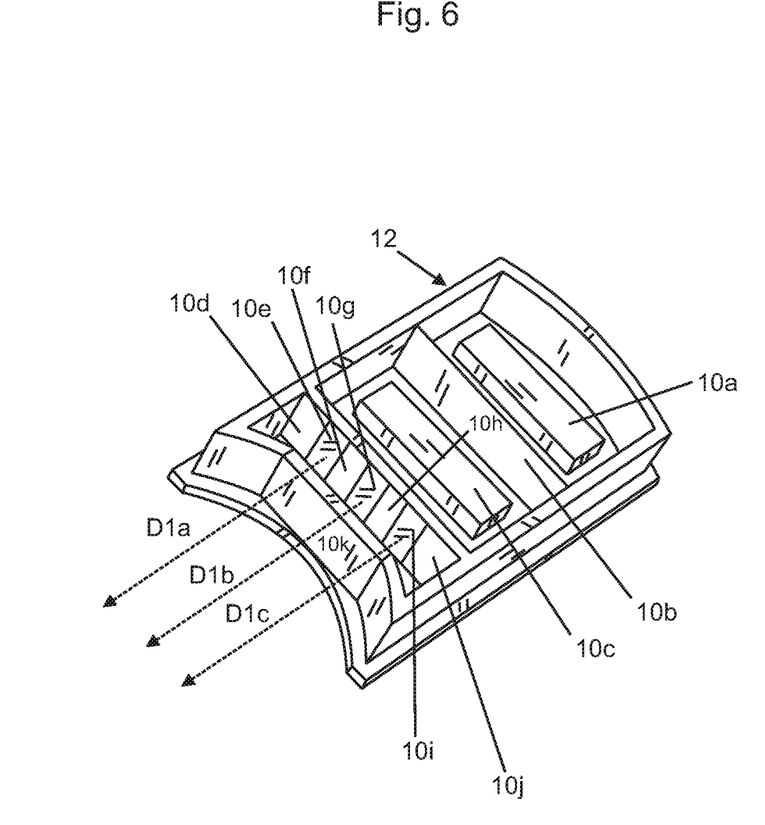
FIG. 6 shows a front, right, and bottom perspective view of the housing of FIG. 5, with various internal components shown in simplified form.

FIG. 6 shows a front, right, and bottom perspective view of the housing 12 of FIG. 5, with various internal components. FIG. 6 shows 10a, which may be a a rechargeable lithium ion battery or other battery or power source, a wall 10b, a circuit board with various components 10c shown further in block diagram format in FIG. 8, LEDs 10e, 10g, and 10i, which emit light, such as UVC light in at least directions D1a, D1b, and D1c through a lens 10k. In addition, there are reflecting surfaces 10d, 10f, 10h, and 10j, which may serve to concentrate the light from LEDs 10e, 10g, and 10i, in the directions D1a, D1b, and D1c.

Figure 7:
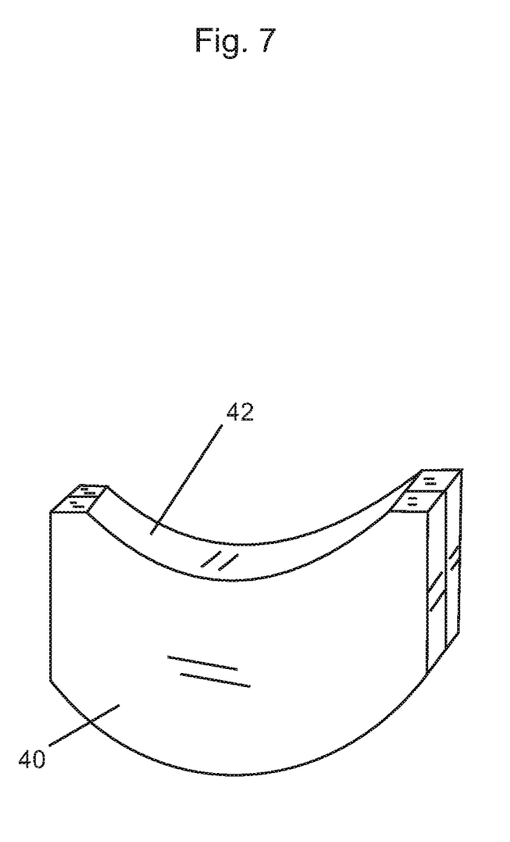
FIG. 7 shows a front, top, and right perspective view of the first apparatus which reflects light.

FIG. 7 shows a front, top, and right perspective view of the first apparatus which reflects light 40, and the reflecting or mirror surface 42.

Figure 8:
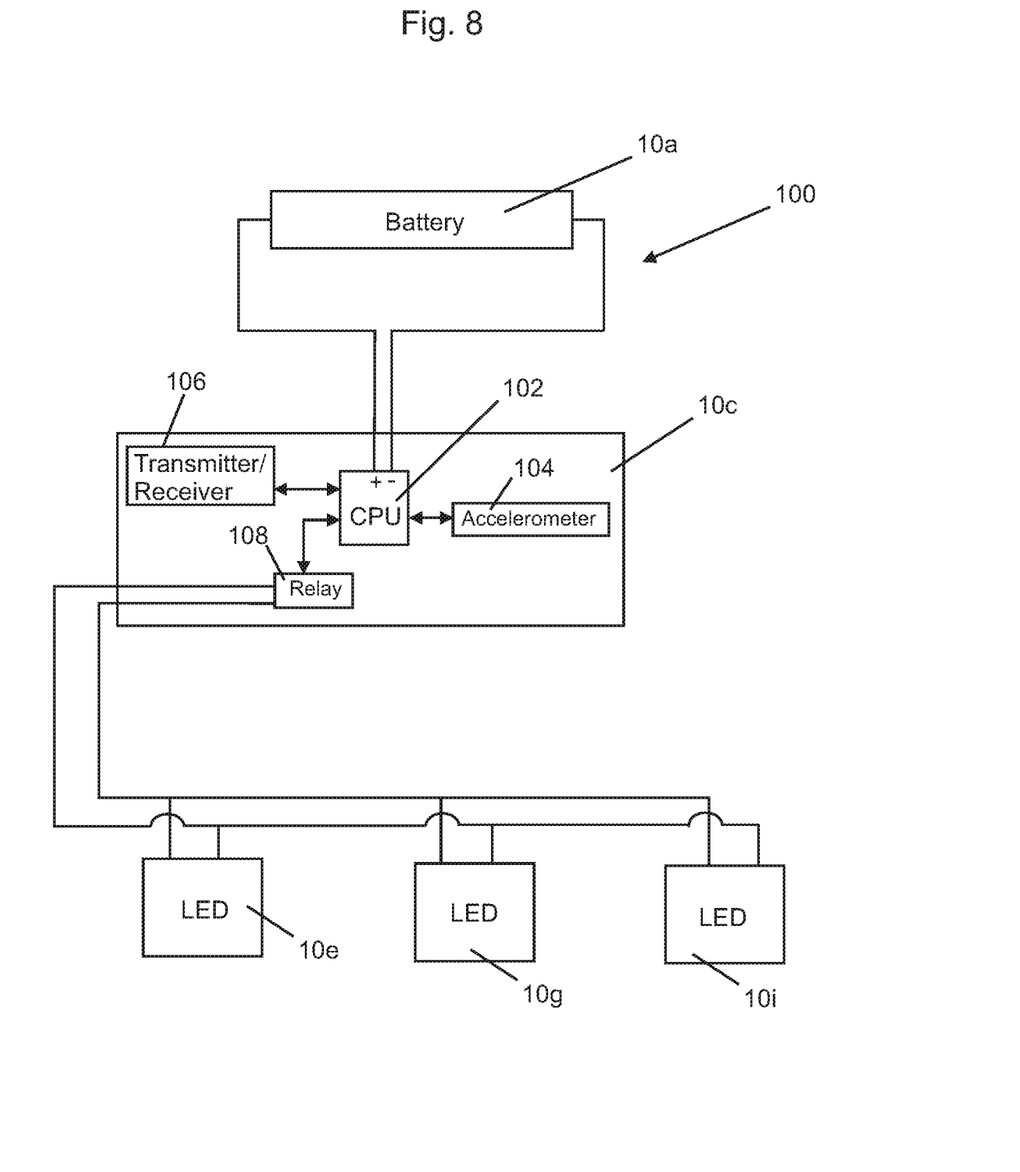
FIG. 8 shows a block diagram of components for the first apparatus which produces light.

FIG. 8 shows a block diagram 100 of components for the first apparatus which produces light 10. The first apparatus which produces light 10, may include battery 10a, CPU, central processing unit or computer processor 102, accelerometer 104, transmitter/receiver 106, relay 108, and LEDs 10e, 10g, and 10i.

The battery 10a may be a lithium ion rechargeable battery. The transmitter/receiver 106 may be a Bluetooth device which provides wireless communications. The accelerometer 104 does upon detecting movement of the door 2 in FIG. 1, produces a door movement signal to the CPU 102. In response to the door movement signal, the CPU 102 causes the LEDs 10e, 10g, and 10i (or some other light source, typically for producing UVC light for disinfecting) to activate and to thereby produce and emanate light from opening 11e towards door knob 20, then to reflecting surface 42 of apparatus 40, which reflects light back towards the door knob 20. The light, typically UVC light, disinfects, or substantially disinfects the the door knob 20.

The relay 108 is connected to the LEDs 20e, 20g, 20i, and can be a manual switch for allowing the LEDs 20e, 20g, and 20i to turn on when activated by the accelerometer.

Figure 9:
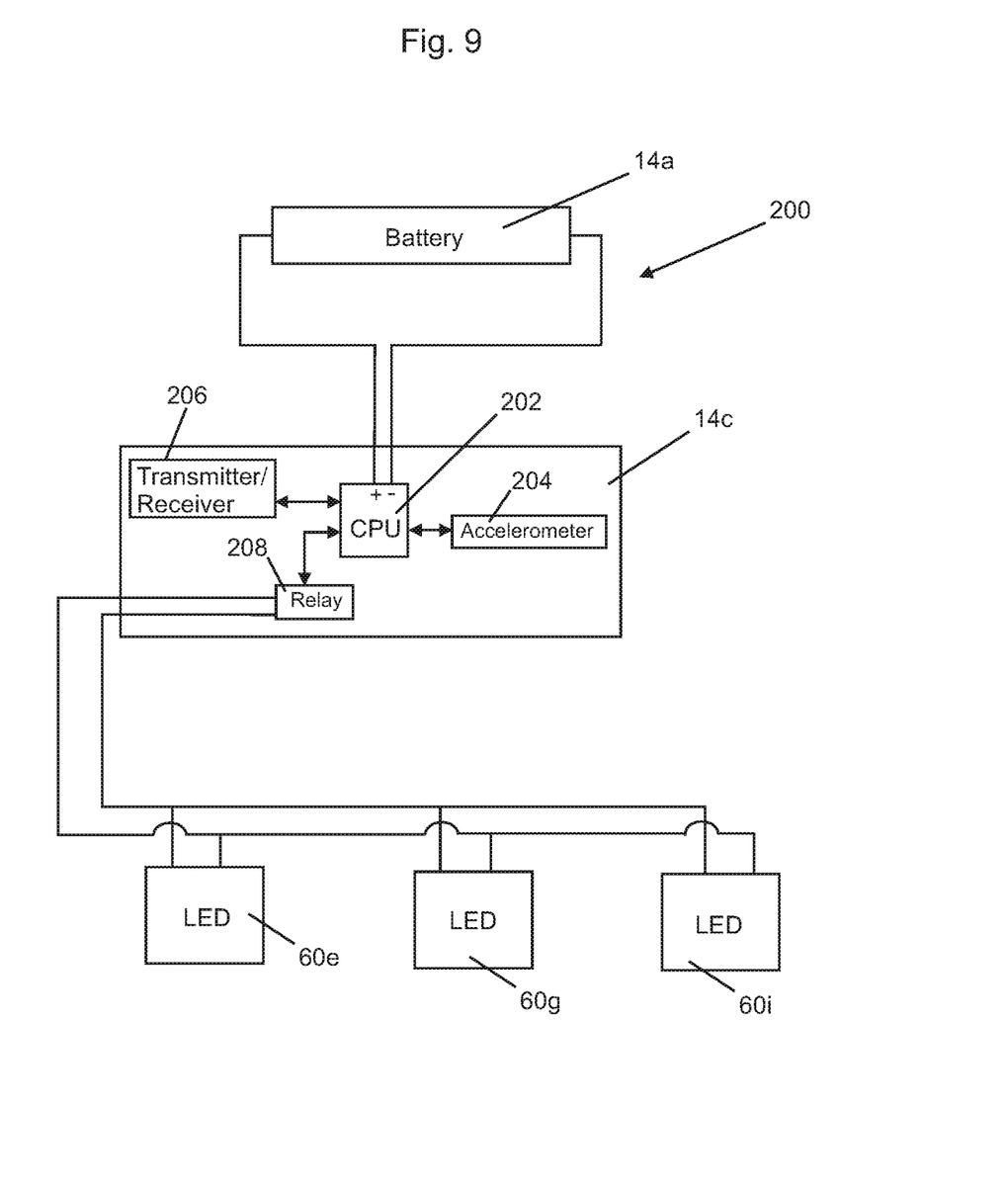
FIG. 9 shows a block diagram of components for the second apparatus which produces light.

FIG. 9 shows a block diagram 200 of components for the second apparatus which produces light 14. The second apparatus which produces light 14, may include battery 14a, a block of components 10c, which includes CPU, central processing unit or computer processor 202, accelerometer 204, transmitter/receiver 206, relay 208, and LEDs 60e, 60g, and 60i.

The battery 14a may be a lithium ion rechargeable battery. The transmitter/receiver 206 may be a Bluetooth device which provides wireless communications. The accelerometer 204 does upon detecting movement of the door 2 in FIG. 1, produces a door movement signal to the CPU 202. In response to the door movement signal, the CPU 202 causes the LEDs 60e, 60g, and 60i (or some other light source, typically for producing UVC light for disinfecting) to activate and to thereby produce and emanate light from opening, analogous to opening 11e, for first apparatus 10, towards door knob 30, then to reflecting surface 52 of apparatus 50, which reflects light back towards the door knob 30. The light, typically UVC light, disinfects, or substantially disinfects the the door knob 30.

The relay 208 is connected to the LEDs 60e, 60g, 60i, and can be a manual switch for allowing the LEDs 60e, 60g, and 60i to turn on when activated by the accelerometer.

The first apparatus for producing light 10 may communicate with the second apparatus for producing light 14 via transmitter/receiver 106 in FIG. 8 and transmitter/receiver 206 in FIG. 9. The first apparatus for producing light 10 may be programmed in its CPU 102, to be a master device and the second apparatus for producing light 14, in its CPU 202 may be programmed to be a servant device. The CPU 202 and accelerometer 204 are optional on the servant device, if desired, as a simple controller or simplified CPU 202 can replace these components to relay the signal from the Transmitter/Receiver 206 to the LEDs 60e, 60g, and 60i, to activate the LEDs 60e, 60g, and 60i to disinfect the door knob 30 or at least a large portion of the door knob 30. The CPU or computer processor 102 may communicate with the CPU 202 or a simplified version of the CPU 202, via the transmitters/receivers 106 and 206, to cause the CPU 202 to activate the LEDs 60e, 60g, and 60i.

A sequence of operations may be executed in accordance with one or more embodiments of the present invention.

In an activation mode, the accelerometer 104 of component 10c of the first apparatus for producing light 10 may detect a force of the opening or closing of the door 2. The CPU 102 may include a computer processor and computer memory, and may have stored in the computer memory a minimum threshold value for a minimum threshold signal corresponding to a minimum threshold force to be detected by the accelerometer. The detected minimum force indicates that the door 2 has been operated.

A detected signal from the accelerometer, due to a force or movement of the door 2, is sent to the CPU 102 and the computer processor of the CPU 102 compares the signal to the stored minimum threshold value in computer memory of the CPU 102. If the value of the signal, such as the amplitude, exceeds the stored minimum value in computer memory, then the CPU 102 starts a programmed sequence, wherein instructions for the programmed sequence are stored in computer memory of the CPU 102.

The CPU 102, as programmed, initiates a delay, which may be five seconds, to allow a person for example, touch the door knob 20, open the door 2, touch the door knob 30, and close the door 2. I.e. The CPU 102 waits until a person's hand is not touching the door knob 20 or 20, and then activates the LEDs 10e, 10g, and 10i, and the LEDs 60e, 60g, and 60i, to disinfect the door knobs 20 and 30.

In at least one embodiment the LEDs 10e, 10g, 10i, 60e, 60g, and 60i are activated and remain in an on state for twenty seconds to thoroughly disinfect the door knobs 20 and 30.

The CPU 102 may send a signal via transmitter/receiver 106 and transmitter receiver 206 to cause the LEDs 60e, 60g, and 60i to be activated and on at the same time as the LEDs 10e, 10g, and 10i. The transmitter/receivers 106 and 206 may be or may be replaced by Bluetooth (trademarked) or for example, some other short range wireless devices.

The CPU 202 may be simplified to be a relay or may be replaced by a relay which detects a control signal from the CPU 102, such as via voltage, and activates LEDs 60e, 60g, and 60i, and causes them to remain on for twenty seconds as a result of transmission of signal from CPU 102 for twenty seconds, or as a result of the CPU 202 causing activation to continue for twenty seconds after receiving a start signal.

In at least one embodiment the LEDs 10e, 10g, 10i, and 60e, 60g, and 60i may remain on for twenty seconds and then all shut off.

The apparatus for producing light 10, which may be a master unit, may then enter a secondary mode for up to thirty minutes as programmed in a computer memory of the CPU 102.

In at least one embodiment, when the secondary mode, if the accelerometer 104 detects a force of the opening or closing of the door, i.e. by producing a signal having for example an amplitude greater than a minimum threshold value as programmed in computer memory of the CPU 102, then the the previous activation mode process may be repeated. I.e. five second delay (or some other appropriate delay) to allow the person to open and close the door, and then a disinfecting state for twenty seconds, or some other appropriate time period.

Following the secondary mode, the master unit, or the first apparatus for producing light 10 may enter a standby mode. In at least one embodiment, if the first apparatus for producing light 10 is in secondary mode for over thirty minutes, without the completion of the cycle, the master unit or the first apparatus for producing light 10 may revert back to standby mode.

In standby mode, the first apparatus for producing light 10 may wait for detection of any motion of opening or closing the door 2 that exceeds a minimum threshold. In addition, in at least one embodiment, a computer processor of the CPU 102 may be programmed to activate the LEDs 10e, 10g, 10i, 60e, 60g, and 60i for twenty seconds, or an appropriate period of time, to substantially disinfect the door knobs 20 and 30, if no signal exceeding the threshold has been received from the accelerometer 104 in six hours. For example, if the door 2 has not been used in six hours, or some other reasonable time period of non use, the CPU 102 may be automatically programmed to disinfect or substantially disinfect the door knobs 20 and 30. After disinfecting, the CPU 102 may again enter into standby mode.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A method comprising the steps of:
    projecting a first light from a first apparatus that produces light towards a first doorknob on a first side of a door in response to a first movement of the door;
    projecting a second light from a second apparatus that produces light towards a second doorknob on a second side of the door in response to the first movement of the door;
    wherein the first side of the door is opposite the second side of the door;
    wherein the first light is short wavelength ultraviolet light;
    wherein the first apparatus that produces light is located on the first side of the door and the second apparatus that produces light is located on the second side of the door; and
    wherein the first apparatus that produces light includes a computer processor, which is programmed to make the first apparatus that produces light a master device and the second apparatus that produces light a servant device of the master device, so that the first apparatus that produces light sends a signal to cause the second apparatus that produces light to project the second light without any input from any device located on the second side of the door.

* * * * *